(12) United States Patent
Mihalcea et al.

(10) Patent No.: US 8,735,115 B2
(45) Date of Patent: *May 27, 2014

(54) METHOD FOR CONTROLLING THE SULPHUR CONCENTRATION IN A FERMENTATION METHOD

(71) Applicant: LanzaTech New Zealand Limited, Auckland (NZ)

(72) Inventors: Christophe Daniel Mihalcea, Auckland (NZ); Prana Haryanto, Auckland (NZ); Sean Dennis Simpson, Auckland (NZ)

(73) Assignee: LanzaTech New Zealand Limited, Auckland (NZ)

(*) Notice: Subject to any disclaimer, the term of this patent is extended or adjusted under 35 U.S.C. 154(b) by 0 days.

This patent is subject to a terminal disclaimer.

(21) Appl. No.: 13/851,772

(22) Filed: Mar. 27, 2013

(65) Prior Publication Data

US 2013/0260429 A1    Oct. 3, 2013

Related U.S. Application Data

(60) Provisional application No. 61/618,207, filed on Mar. 30, 2012.

(51) Int. Cl.
*C12P 7/06* (2006.01)

(52) U.S. Cl.
USPC ............................................... 435/161

(58) Field of Classification Search
USPC .................................. 435/161, 244, 253.6
See application file for complete search history.

(56) References Cited

U.S. PATENT DOCUMENTS

| | | | |
|---|---|---|---|
| 5,173,429 A | 12/1992 | Gaddy et al. | |
| 5,593,886 A | 1/1997 | Gaddy | |
| 5,807,722 A | 9/1998 | Gaddy | |
| 5,821,111 A | 10/1998 | Grady et al. | |
| 6,136,577 A | 10/2000 | Gaddy | |
| 6,340,581 B1 | 1/2002 | Gaddy | |
| 6,368,819 B1 | 4/2002 | Gaddy et al. | |
| 7,078,201 B2 | 7/2006 | Burmaster | |
| 8,119,378 B2* | 2/2012 | Simpson et al. | 435/161 |
| 2011/0059499 A1 | 3/2011 | Simpson et al. | |
| 2011/0212433 A1* | 9/2011 | Barker et al. | 435/3 |
| 2011/0300593 A1* | 12/2011 | Mihalcea et al. | 435/140 |
| 2013/0230894 A1* | 9/2013 | Mihalcea et al. | 435/158 |

FOREIGN PATENT DOCUMENTS

| | | |
|---|---|---|
| EP | 117309 | 5/1984 |
| WO | WO 98/00558 | 1/1998 |
| WO | WO 00/68407 | 11/2000 |
| WO | WO 02/08438 | 1/2002 |
| WO | WO2007/117157 | 10/2007 |
| WO | WO/2008/028055 | 3/2008 |
| WO | WO2008/115080 | 9/2008 |
| WO | WO2009/022925 | 2/2009 |
| WO | WO2009/064200 | 5/2009 |
| WO | 2012015318 | 2/2012 |

OTHER PUBLICATIONS

Aribini et al, Archives of Microbiology 161, pp. 345-351 (1994).
Drake, Küsel, and Matthies, The Prokaryotes, Acetogenic Prokaryotes, Chapter 1.13 (2006), Springer, DOI:10.1007/0-387-30742-7_13.
Liou et al., International Journal of Systematic and Evolutionary Microbiology, 55: pp. 2085-2091(2005); DOI: 10.1099/ijs.0.63482-0.
Sakai et al, Biotechnology Letters, 26: pp. 1607-1612 (2004).
Svetlichny, V.A., Sokolova, T.G. et al , Systematic and Applied Microbiology; 14, pp. 254-260(1991).
Simpa et. al. Critical Reviews in Biotechnology, vol. 26. pp. 41-65 (2006).

* cited by examiner

*Primary Examiner* — Ralph Gitomer
(74) *Attorney, Agent, or Firm* — Frank S Molinaro (57) ABSTRACT

This invention relates generally to methods for increasing the efficiency of microbial growth and production of products, such as alcohols and acids by microbial fermentation of substrates containing carbon monoxide. More particularly the invention relates to the provision of an alternative sulphur source to a liquid nutrient medium, such that sulphur is available to one or more microorganisms of the fermentation.

11 Claims, 3 Drawing Sheets

| Name | Oxidation No. | Utilized |
|---|---|---|
| H₂SO₄ | +6 | No |
| Na₂S₂O₆ | +5 | No |
| H₂SO₃ | +4 | Yes |
| Na₂S₂O₄ | +3 | Yes |
| Na₂S₂O₃ | +2 | No |
| S₈ | 0 | Yes |
| RSSR (cystine) | -1 | No |
| Na₂S/NaHS/cysteine | -2 | Yes |

FIG. 5

| day | mL 0.2M (NH₄)₂SO₄ / media | mmol (NH₄)₂SO₄ | Dilution rate | CO uptake (mmol/L/min) | Biomass (g/L) | ppm H₂S (headspace) |
|---|---|---|---|---|---|---|
| | 12 | 1.5 | 2.08 | 7.5 | 6 | 90 |
| | 22 | 2.7 | 2.64 | 9 | 8 | 90 |
| | 29 | 3.4 | 2.7 | 11 | 8 | 70 |

FIG. 6

| day | mL 0.2M (NH₄)₂SO₄ / media | mmol (NH₄)₂SO₄ | Dilution rate | CO uptake (mmol/L/min) | Biomass (g/L) | ppm H₂S (headspace) |
|---|---|---|---|---|---|---|
| | 10 | 1.2 | 2.2 | 6.8 | 6.5 | 80 |
| | 15 | 1.8 | 2.6 | 7.5 | 8 | 90 |

FIG. 7

METHOD FOR CONTROLLING THE SULPHUR CONCENTRATION IN A FERMENTATION METHOD

CROSS REFERENCE TO RELATED APPLICATIONS

This application claims priority of provisional application 61/618,207 filed on 30 Mar. 2012 the contents of which are incorporated in their entirety by reference.

FIELD OF THE INVENTION

This invention relates generally to methods for increasing the efficiency of microbial growth and production of products, such as alcohols and acids by microbial fermentation. More particularly the invention relates to processes for producing alcohols, particularly ethanol, by microbial fermentation of substrates containing carbon monoxide.

BACKGROUND OF THE INVENTION

Ethanol is rapidly becoming a major hydrogen-rich liquid transport fuel around the world. Worldwide consumption of ethanol in 2002 was an estimated 10.8 billion gallons. The global market for the fuel ethanol industry has also been predicted to grow sharply in future, due to an increased interest in ethanol in Europe, Japan, the USA and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, or as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major free energy-rich by-product of the incomplete combustion of organic materials such as coal or oil and oil derived products. For example, the steel industry in Australia is reported to produce and release into the atmosphere over 500,000 tonnes of CO annually.

It has long been recognised that catalytic processes may be used to convert gases consisting primarily of CO and/or CO and hydrogen ($H_2$) into a variety of fuels and chemicals. However, micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as their sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Aribini et al, Archives of Microbiology 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to Green House Gas emissions.

The importance of controlling parameters of the liquid nutrient medium used for culturing bacteria or micro-organisms within a bioreactor used for fermentation has been recognised in the art. NZ 556615, filed 18 Jul. 2007 and incorporated herein by reference, describes, in particular, manipulation of the pH and the redox potential of such a liquid nutrient medium. For example, in the culture of anaerobic acetogenic bacteria, by elevating the pH of the culture to above about 5.7 while maintaining the redox potential of the culture at a low level (−400 mV or below), the bacteria convert acetate produced as a by-product of fermentation to ethanol at a much higher rate than under lower pH conditions. NZ 556615 further recognises that different pH levels and redox potentials may be used to optimise conditions depending on the primary role the bacteria are performing (i.e., growing, producing ethanol from acetate and a gaseous CO-containing substrate, or producing ethanol from a gaseous containing substrate).

U.S. Pat. No. 7,078,201 and WO 02/08438 also describe improving fermentation processes for producing ethanol by varying conditions (e.g. pH and redox potential) of the liquid nutrient medium in which the fermentation is performed.

The pH of the liquid nutrient medium may be adjusted by adding one or more pH adjusting agents or buffers to the medium. For example, bases such as NaOH and acids such as sulphuric acid may be used to increase or decrease the pH as required. The redox potential may be adjusted by adding one or more reducing agents (e.g. methyl viologen) or oxidising agents.

Similar processes may be used to produce other alcohols, such as butanol, as would be apparent to one of skill in the art.

Regardless of the source used to feed the fermentation reaction, problems can occur when there are breaks in the supply. More particularly, such interruptions can be detrimental to the efficiency of the micro-organisms used in the reaction, and in some cases, can be harmful thereto. For example, where CO gas in an industrial waste gas stream is used in fermentation reactions to produce acids/alcohols, there may be times when the stream is not produced. During such times, the micro-organisms used in the reaction may go into hibernation. When the stream is available again, there may then be a lag before the micro-organisms are fully productive at performing the desired reaction.

Sulphur sources such as cysteine and/or sulfide are also used to attain desirable ORP (oxidation-reduction potential) of the anaerobic fermentation broth prior to inoculation. However, such reducing agents are slow and have limited reducing power. Furthermore, when these sulphur containing compounds are used to reduce ORP of a fermentation media, they are oxidised themselves. For example, cysteine is oxidised to the dimer cystine. It is considered that the reduced form of these compounds is substantially more bioavailable as a sulphur source for consumption by a microbial culture than the oxidised form. As such, when a sulphur source is used to lower the ORP of a fermentation reaction, the actual concentration of sulphur available to the microbial culture will decrease. Accordingly, identification of an improved or alternative reducing agent for use with anaerobic fermentation systems using carbon monoxide containing gases as a feedstock, is a key component in ensuring high alcohol production rates and low process operating costs.

Along with main nutrients such as nitrogen and phosphorus, sulphur plays an important role in the fermentation of the anaerobe *C. autoethanogenum*. Sulphur is essential for the microbe and is needed for a range of compounds and enzymes that allow *C. autoethanogenum* fermentation of CO into acetic acid, ethanol and butanediol and to generate ATP for growth of biomass. Sulphur is part of a class of biological compounds called ferredoxins and is an integral part of many of the Wood-Ljungdahl enzymes that fix gaseous CO into acetyl-Co-A. Generally the most reduced form of sulphur is assimilated into functional proteins. The microbe can take up $H_2S$ directly or in the form of the hydrogensulfide ion and assimilate it into the desired proteins. Many of the microbes sulphur containing enzymes also contain transition metal ions such as $Fe^{2+}$, $Zn^{2+}$, $Co^{2+}$ and $Mn^{2+}$. As sulphides of these metals have very low solubility products at pH values around neutral, free $H_2S$ and or free transition metals are usually scarce in such habitats, because the majority of the metal ions will be bound into insoluble metal sulphides and are therefore not accessible to the microbes.

It is an object of the present invention to provide a system and/or a process that goes at least some way towards overcoming the above disadvantages, or at least to provide the public with a useful choice.

SUMMARY OF THE INVENTION

In one broad aspect, the invention provides a method of improving growth efficiency of a bacterial culture, the method comprising the step providing an alternative sulphur source to the culture.

In a second broad aspect, there is provided a method of maintaining or increasing production rates of one or more products produced by a microbial culture, the method comprising the step of providing an alternative sulphur source to the culture.

In a third broad aspect, there is provided a method of improving fermentation efficiency of a bacterial culture, the method comprising the step of providing an alternative sulphur source to the culture.

In a fourth aspect there is provided a method of producing one or more products by microbial fermentation, the method comprising;
  i. providing a gaseous substrate comprising CO to a bioreactor comprising a culture of one or more carboxydotrophic microorganisms in a liquid nutrient medium;
  ii. anaerobically fermenting the substrate to produce one or more products selected from the group comprising alcohols, acids and mixtures thereof; and
  iii. recovering one or more products.

In one embodiment the liquid nutrient medium comprises at least one sulphur source selected from the group comprising $SO_2$, $H_2SO_3$, $Na_2S_2O_4$, $S_8$, $Na_2S$, NaHS, cysteine, $NH_4HSO_3$ or $(NH_4)_2SO_3$.

According to one embodiment of the invention, there is provided a method for improving efficiency of microbial fermentation of a substrate comprising CO, the method including providing an alternative sulphur source to a nutrient medium, such that sulphur is available to one or more microorganisms.

In particular embodiments of the above aspects, the alternative sulphur source is selected from the group comprising sulphurous acid ($H_2SO_3$), $Na_2S_2O_4$, $S_8$, $Na_2S$, NaHS, $SO_2$, cysteine, $NH_4HSO_3$ or $(NH_4)_2SO_3$. In particular embodiments the alternative sulphur source is sulphurous acid.

In particular embodiments of the above aspects the sulphur source is a waste product of an industrial process. The industrial process may include but is not limited to coal combustion or oil combustion by power plants.

In particular embodiments, the one or more sulphur containing species can be utilised by a microbial culture.

In another broad aspect, the present invention provides a method of producing one or more acid and/or alcohol by microbial fermentation, the method comprising the steps of:
  i. providing a substrate comprising carbon monoxide and optionally carbon dioxide and/or hydrogen;
  ii. in a bioreactor containing a culture of one or more micro-organisms anaerobically fermenting the substrate to produce one or more products consisting of acids and/or alcohols; and
  iii. capturing and recovering the one or more products produced;
wherein the culture is provided with sulphurous acid as a sulphur source.

In particular embodiments of the various aspects, the substrate comprising CO is gaseous. In particular embodiments, the gaseous substrate comprises a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. In a particular embodiment, the gaseous substrate comprises a gas obtained from a steel mill.

In certain embodiments, the CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In particular embodiments, the alcohol produced by the fermentation process is ethanol. The fermentation reaction may also produce acetate.

In certain embodiments of the various aspects the sulphur source is selected from the group comprising $SO_2$, $H_2SO_3$, $Na_2S_2O_4$, $S_8$, $Na_2S$, NaHS, cysteine, $NH_4HSO_3$ or $(NH_4)_2SO_3$. In certain embodiments the sulphur source is sulphurous acid. In certain embodiments, the sulphur source is $(NH_4)_2SO_3$. In certain embodiments the concentration of $(NH_4)_2SO_3$ is maintained at between 1 mmol and 2.5 mmol.

In certain embodiments, there is a correlation between the amount of the sulphur source provided to the culture and the amount of $H_2S$ present in a headspace of the fermentation vessel/bioreactor. In certain embodiments, the H2S is monitored as an indicator of the sulphur concentration in the fermentation.

In certain embodiments the concentration of $H_2S$ in the headspace is maintained at between 1 ppm and 100 ppm. In certain embodiments increasing the amount of sulphur source provided to the culture increases the $H_2S$ concentration in the headspace, and conversely decreasing the amount of sulphur source provided to the culture decreases the $H_2S$ concentration in the headspace.

In one embodiment, the microorganism is selected from the group of acetogenic carboxydotrophic organisms comprising the species *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Acetobacterium woodii, Alkalibaculum bacchii, Moorella thermoacetica, Sporomusa ovate, Butyribacterium methylotrophicum, Blautia producta, Eubacterium limosum, Thermoanaerobacter kiuvi.*

In particular embodiments, the microorganism is selected from the group of acetogenic carboxydotrophic microorganism comprising the species *Clostridium autoethanogenum, Clostridium ljungdahlii, Clostridium ragsdalei, Clostridium coskatii* and *Clostridium carboxydivorans*. In one embodiment, the acetogenic bacterium is *Clostridium autoethanogenum*.

In one embodiment the fermentation reaction is carried out by *Clostridium autoethanogenum* strain deposited at the German Resource Centre for Biological Material (DSMZ) under the identifying deposit number 19630.

In one embodiment the fermentation reaction is carried out by *Clostridium autoethanogenum* strain deposited at the German Resource Centre for Biological Material (DSMZ) under the identifying deposit number DSM 23693.

In particular embodiments the sulphur source is a waste product of an industrial process. In certain embodiments the sulphur source is a waste product of a coal manufacturing process.

Although the invention is broadly as defined above, it is not limited thereto and also includes embodiments of which the following description provides examples.

BRIEF DESCRIPTION OF THE DRAWINGS

The invention will now be described in more detail and with reference to the accompanying figures, in which.

DETAILED DESCRIPTION OF THE INVENTION

Sulphur Source

The optimal pH of *C. autoethanogenum* fermentation is around pH 5. At pH 5, $S^{2-}$ is predominately protonated and exits mainly as $H_2S$ (which is a dissolved gas) and small amounts of $HS^-$. The former gas is removed from the bioreactor by sparging the feed gases through the system. For this reason it is necessary to store $H_2S$ containing aqueous solutions at high pH values to trap the sulphur in the form of the sulphide ion and only drop small volumes of the solution into the fermentation vessel to avoid losing the sulphur from the system before it can be utilised by the microbe. Such high pH solutions are very corrosive and also tend to form precipitates with the majority of elements either by forming insoluble sulphides or by precipitating insoluble hydroxides. The corrosive and precipitate nature of the solution requires that there is a strict separation of this solution and other media components.

Figure 5:
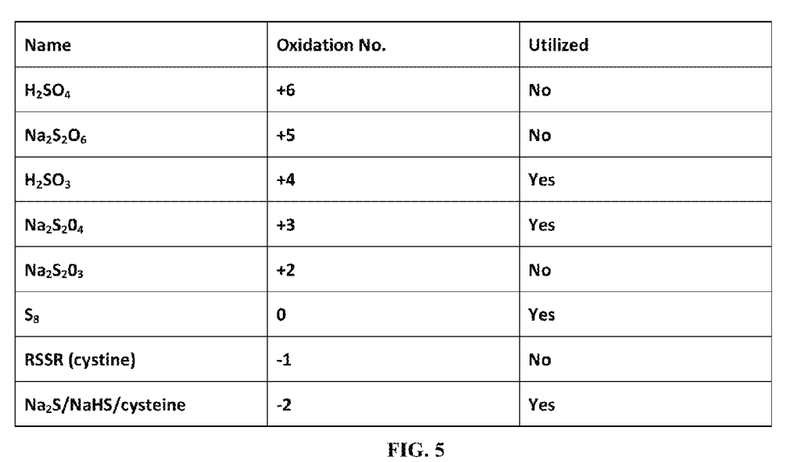
FIG. 5 shows the oxidation numbers of various alternative sulphur sources.

To remedy these problems, a number of alternative sulphur sources have been identified and tested, to determine the ability of *C. autoethanogenum* to utilize these sulphur sources. FIG. 5 shows a number of sulphur compounds, their oxidation numbers, and the ability of *C. autoethanogenum* to utilize them.

Sulphurous acid ($H_2SO_3$) has been identified as an alternative sulphur source. Sulphurous acid is a much stronger acid than $H_2S$, and at pH 5 the acid will be quantitatively deprotonated and stay in solution as the bisulphite ion. Aqueous solutions can therefore be stored in the pH range without the additional issue of hydroxide precipitation or extensive corrosion. Dosing the sulphur into the bioreactor is also easier as the microbes convert $SO_2$ inside the cell into the $H_2S$ needed for anabolism. $H_2S$ losses through sparging other feeding gases can be minimised this way. Sulphur in the form of sulphurous acid, $H_2SO_3$ or $NH_4HSO_3$ or $(NH_4)_2SO_3$ can be mixed into the media prior the nutrient medium being provided to the bioreactor. This increases the efficiency of the fermentation, by eliminating the need for a pump system and control loop required for the continual addition of $H_2S$ in previous systems.

Additionally it has been identified that using sulphurous acid, $H_2SO_3$ or $NH_4HSO_3$ or $(NH_4)_2SO_3$ as a sulphur source eliminates the need to separate the solution from other media components. At pH6, the solution is close to neutral and the solutions are colourless and clear and emit no gases, which makes storing them very easy. Another advantage is that $NH_4^+$ and $Na^+$ bisulphites (the hydrogen containing salts of sulphurous acid) dissolve very easily in solution.

Sulphurous acid has been found to be toxic to most microorganisms. The inventors have surprisingly found that by controlling the rate of addition of sulphurous acid to the fermentation broth, the microbial culture is able to utilise sulphurous acid as a sulphur source, without detriment to the growth and production of the culture.

The inventors have identified that overloading the culture with sulphurous acid is detrimental and can cause the death of the culture. To overcome this problem the sulphurous acid is added gradually to the fermentation. In certain embodiments, the sulphurous acid is added in a drop like continuous manner to the fermentation. Due to the toxicity of sulphurous acid at high concentrations it is necessary to monitor the amount of sulphurous acid provided to the culture and adjust the flow of the acid to the bioreactor if the amount of sulphurous acid available to the culture rises above or drops below a predetermined range.

The sulphur source in the form of sulphurous acid is quickly taken up by the microbial culture. The conversion of sulphurous acid by the microbial culture results in the production of H2S which is released into the head space of the bioreactor. The flow rate of sulphurous acid provided to the bioreactor can be controlled by monitoring the H2S concentration in the headspace of the bioreactor. High levels of H2S in the headspace are indicative of high concentrations of sulphurous acid in the liquid nutrient medium. Given the toxicity of sulphurous acid at high concentrations is desirable to control the concentration of sulphurous acid in the liquid nutrient medium. In certain embodiments of the invention, it has been found to be desirable to maintain the H2S concentration in the headspace at less than 500 ppm, or less than 300 ppm, or less than 200 ppm, or less than 150 ppm, or less than 100 ppm, or less than 80 ppm, or less than 50 ppm. In certain embodiments, the H2S concentration in the headspace is maintained at around 100 ppm. In certain embodiments the H2S concentration in the headspace is maintained within a range of around 10 ppm to around 100 ppm. In certain embodiments the H2S concentration in the headspace is maintained within a range of 60 ppm to 100 ppm. In certain embodiments the H2S concentration in the headspace is maintained within a range of about 70 ppm to about 90 ppm.

$SO_2$ gas is a waste product of coal power plants and it has been the cause of environmental problems in the form of acid rain. Coal power plants now have to filter their sulphur emission and treaties are made to reduce said pollution. The ability of *C. autoethanogenum* to utilise $SO_2$ enables the capture and utilisation of waste products.

The Bioreactor

The fermentation may be carried out in any suitable bioreactor, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor may be fed and in which most of the fermentation product (e.g. ethanol and acetate) may be produced. The bioreactor of the present invention is adapted to receive a CO and/or $H_2$ containing substrate.

The CO and/or $H_2$ Containing Substrate

The CO and/or $H_2$ containing substrate is captured or extracted from the process using any convenient method. Depending on the composition of the CO and/or $H_2$ containing substrate, it may also be desirable to treat it to remove any undesired impurities, such as dust particles before introducing it to the fermentation. For example, the substrate may be filtered or scrubbed using known methods.

The substrate comprising CO, preferably a gaseous substrate, may be obtained as a by-product of any step of the steam reforming process. Such steps include the steam reforming step, the WGS step and the PSA step as described herein.

Typically, the CO will be added to the fermentation reaction in a gaseous state. However, methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemistry and Biotechnology* Volume 101, Number 3/October, 2002) could be used for this purpose. Where a "gas stream" is referred to herein, the term also encompasses other forms of transporting the gaseous components of that stream such as the saturated liquid method described above.

Gas Compositions

The CO-containing substrate may contain any proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 2%, may also be appropriate, particularly when $H_2$ and $CO_2$ are also present.

The presence of $H_2$ should not be detrimental to hydrocarbon product formation by fermentation. In particular embodiments, the presence of hydrogen results in an improved overall efficiency of alcohol production. For example, in particular embodiments, the substrate may comprise an approximate 2:1, or 1:1, or 1:2 ratio of $H_2$:CO. In other embodiments, the CO containing substrate comprises less than about 30% $H_2$, or less than 27% $H_2$, or less than 20% $H_2$, or less than 10% $H_2$, or lower concentrations of $H_2$, for example, less than 5%, or less than 4%, or less than 3%, or less than 2%, or less than 1%, or is substantially hydrogen free. In still other embodiments, the CO containing substrate comprises greater than 50% H2, or greater than 60% H2, or greater than 70% H2, or greater than 80% H2, or greater than 90% H2.

The substrate may also contain some $CO_2$ for example, such as about 1% to about 80% $CO_2$ by volume, or 1% to about 30% $CO_2$ by volume.

Blending of Streams

It may be desirable to blend a reformed substrate stream comprising CO and H2 with one or more further streams in order to improve efficiency, alcohol production and/or overall carbon capture of the fermentation reaction. Without wishing to be bound by theory, in some embodiments of the present invention, carboxydotrophic bacteria convert CO to ethanol according to the following:

However, in the presence of H2, the overall conversion can be as follows:

Accordingly, streams with high CO content can be blended with reformed substrate streams comprising CO and H2 to increase the CO:H2 ratio to optimise fermentation efficiency. By way of example, industrial waste streams, such as off-gas from a steel mill have a high CO content, but include minimal or no H2. As such, it can be desirable to blend one or more streams comprising CO and H2 with the waste stream comprising CO, prior to providing the blended substrate stream to the fermenter. The overall efficiency, alcohol productivity and/or overall carbon capture of the fermentation will be dependent on the stoichiometry of the CO and H2 in the blended stream. However, in particular embodiments the blended stream may substantially comprise CO and H2 in the following molar ratios: 20:1, 10:1, 5:1, 3:1, 2:1, 1:1 or 1:2.

In addition, it may be desirable to provide CO and $H_2$ in particular ratios at different stages of the fermentation. For example, substrate streams with a relatively high $H_2$ content (such as 1:2 CO:$H_2$) may be provided to the fermentation stage during start up and/or phases of rapid microbial growth. However, when the growth phase slows, such that the culture is maintained at a substantially steady microbial density, the CO content may be increased (such as at least 1:1 or 2:1 or higher, wherein the $H_2$ concentration may be greater or equal to zero).

Blending of streams may also have further advantages, particularly in instances where a waste stream comprising CO is intermittent in nature. For example, an intermittent waste stream comprising CO may be blended with a substantially continuous reformed substrate stream comprising CO and $H_2$ and provided to the fermenter. In particular embodiments of the invention, the composition and flow rate of the substantially continuous blended stream may be varied in accordance with the intermittent stream in order to maintain provision of a substrate stream of substantially continuous composition and flow rate to the fermenter.

Fermentation

Processes for the production of ethanol and other alcohols from gaseous substrates are known. Exemplary processes include those described for example in WO2007/117157, WO2008/115080, WO2009/022925, WO2009/064200, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

Microorganisms

In various embodiments, the fermentation is carried out using a culture of one or more strains of carboxydotrophic bacteria. In various embodiments, the carboxydotrophic bacterium is selected from *Moorella*, *Clostridium*, *Ruminococcus*, *Acetobacterium*, *Eubacterium*, *Butyribacterium*, *Oxobacter*, *Methanosarcina*, *Methanosarcina*, and *Desulfotomaculum*. A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica*, *Moorella thermoautotrophica*, *Ruminococcus productus*, *Acetobacterium woodii*, *Eubacterium limosum*, *Butyribacterium methylotrophicum*, *Oxobacter pfennigii*, *Methanosarcina barkeri*, *Methanosarcina acetivorans*, *Desulfotomaculum kuznetsovii* (Simpa et. al. Critical Reviews in Biotechnology, 2006 Vol. 26. Pp 41-65). In addition, it should be understood that other acetogenic anaerobic bacteria may be applicable to the present invention as would be understood by a person of skill in the art. It will also be appreciated that the invention may be applied to a mixed culture of two or more bacteria.

In one embodiment, the microorganism is selected from the group of acetogenic carboxydotrophic organisms comprising the species *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, *Acetobacterium woodii*, *Alkalibaculum bacchii*, *Moorella thermoacetica*, *Sporomusa ovate*, *Butyribacterium methylotrophicum*, *Blautia producta*, *Eubacterium limosum*, *Thermoanaerobacter kiuvi*.

These carboxydotrophic acetogens are defined by their ability to utilize and grow chemoautotrophic ally on gaseous one-carbon (C1) sources such as carbon monoxide (CO) and carbon dioxide (CO2) with carbon monoxide (CO) and/or hydrogen (H2) as energy source under anaerobic conditions forming acetyl-CoA, acetate and other products. They share the same mode of fermentation, the Wood-Ljungdahl or reductive acetyl-CoA pathway, and are defined by the presence of the enzyme set consisting of Carbon monoxide dehydrogenase (CODH), Hydrogenase, Formate dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase (CODH/ACS), which combination is characteristic and unique to this type of bacteria (Drake, Kiisel, Matthies, Wood, & Ljungdahl, 2006). In contrast to chemoheterotrophic growth of sugar-fermenting bacteria that convert the substrate into biomass, secondary metabolites and pyruvate from which products are formed (either via acetyl-CoA or directly), in acetogens the substrate is channelled directly into acetyl-CoA, from which products, biomass, and secondary metabolites are formed.

In a one embodiment, the microorganism is selected from a cluster of carboxydotrophic Clostridia comprising the species *C. autoethanogenum*, *C. ljungdahlii*, and "*C. ragsdalei*" and related isolates. These include but are not limited to strains *C. autoethanogenum* JAI-1$^T$ (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), or "*C. ragsdalei* PU$^T$" (ATCC BAA-622) (WO 2008/028055), and related isolates such as "*C. coskatii*" (US patent 2011/0229947), and mutant strains thereof such as *C. ljungdahlii* OTA-1 (Tirado-Acevedo O. Production of Bioethanol from Synthesis Gas Using *Clostridium ljungdahlii*. PhD thesis, North Carolina State University, 2010).

These strains form a subcluster within the Clostridial rRNA cluster I (Collins et al., 1994), having at least 99% identity on 16S rRNA gene level, although being distinct species as determined by DNA-DNA reassociation and DNA fingerprinting experiments (WO 2008/028055, US patent 2011/0229947).

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Köpke et al., 2010) and a GC composition of around 32% mol (Abrini et al., 1994; Köpke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde:ferredoxin oxidoreductase (Köpke et al., 2010, 2011). The organization and number of Wood-Ljungdahl pathway genes, responsible for gas uptake, has been found to be the same in all species, despite differences in nucleic and amino acid sequences (Köpke et al., 2011).

The strains all have a similar morphology and size (logarithmic growing cells are between 0.5-0.7×3-5 µm), are mesophilic (optimal growth temperature between 30-37° C.) and strictly anaerobe (Abrini et al., 1994; Tanner et al., 1993) (WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et al., 1994; Köpke et al., 2011; Tanner et al., 1993)(WO 2008/028055). Indole production has been observed with all species. However, the species differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotroph to certain vitamins (e.g. thiamine, biotin) while others were not.

The traits described are therefore not specific to one organism like *C. autoethanogenum* or *C. ljungdahlii*, but rather general traits for carboxydotrophic, ethanol-synthesizing Clostridia. Thus, the invention can be anticipated to work across these strains, although there may be differences in performance.

In certain embodiments, the microorganism is selected from the group comprising *Clostridium autoethanogenum*, *Clostridium ljungdahlii*, and *Clostridium ragsdalei*. In one embodiment, the group also comprises *Clostridium coskatii*. In one particular embodiment, the parental microorganism is *Clostridium autoethanogenum* DSM23693.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number DSM 23693. In other embodiments, the *Clostridium autoethanogenum* is a *Clostridium autoethanogenum* having the identifying characteristics of DSM deposit number DSM 10061 or DSM 19630. These strains have a particular tolerance to changes in substrate composition, particularly of $H_2$ and CO and as such are particularly well suited for use in combination with a steam reforming process. The address of the German Resource Centre for Biological Material (DSMZ) is DSMZ GmbH Inhoffenstraβe, 7 B, D-38124 Braunschweig, Germany. The microorganism having deposit number DSM 23693 was deposited on 7 Jun. 2010. The microorganism having deposit number DSM 19630 was deposited on 19 Oct. 2007.

Culturing of the bacteria used in the methods of the invention may be conducted using any number of processes known in the art for culturing and fermenting substrates using anaerobic bacteria. By way of example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

Fermentation Conditions

It will be appreciated that for growth of the bacteria and CO-to-hydrocarbon fermentation to occur, in addition to the CO-containing substrate, a suitable liquid nutrient medium will need to be fed to the bioreactor. A nutrient medium will contain vitamins and minerals sufficient to permit growth of the micro-organism used. Anaerobic media suitable for the production of hydrocarbon products through fermentation using CO as the sole carbon source are known in the art. For example, suitable media are described in U.S. Pat. Nos. 5,173,429 and 5,593,886 and WO 02/08438, WO2007/115157 and WO2008/115080 referred to above.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO07/117,157 and WO08/115,080.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of hydrocarbon products. This in turn means that the retention time (defined as the liquid volume in the bioreactor divided by the input gas flow rate) can be reduced when bioreactors are maintained at elevated pressure rather than atmospheric pressure. Also, since a given CO-to-hydrocarbon conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-hydrocarbon fermentation at elevated pressures have also been described elsewhere. For example, WO 02/08438 describes gas-to-ethanol fermentations performed under pressures of 2.1 atm and 5.3 atm, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the hydrocarbon product is consumed by the culture.

Fermentation Products

Methods of the invention can be used to produce any of a variety of hydrocarbon products. This includes alcohols, acids and/or diols. More particularly, the invention may be applicable to fermentation to produce acetate, butyrate, propionate, caproate, ethanol, propanol, butanol, 2,3-butanediol, isopropanol, propylene, butadiene, iso-butylene, and ethylene. These and other products may be of value for a host of other processes such as the production of plastics, pharmaceuticals and agrochemicals. In a particular embodiment, the fermentation product is used to produce gasoline range hydrocarbons (about 8 carbon), diesel hydrocarbons (about 12 carbon) or jet fuel hydrocarbons (about 12 carbon).

The invention also provides that at least a portion of a hydrocarbon product produced by the fermentation is reused in the steam reforming process. This may be performed because hydrocarbons other than $CH_4$ are able to react with steam over a catalyst to produce $H_2$ and CO. In a particular embodiment, ethanol is recycled to be used as a feedstock for the steam reforming process. In a further embodiment, the hydrocarbon feedstock and/or product is passed through a pre-reformer prior to being used in the steam reforming process. Passing through a pre-reformer partially completes the steam reforming step of the steam reforming process which can increase the efficiency of hydrogen production and reduce the required capacity of the steam reforming furnace.

The methods of the invention can also be applied to aerobic fermentations, and to anaerobic or aerobic fermentations of other products, including but not limited to isopropanol.

Product Recovery

The products of the fermentation reaction can be recovered using known methods. Exemplary methods include those described in WO07/117,157, WO08/115,080, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non-volatile and is recovered for re-use in the fermentation.

Acetate, which may be produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used. For example, U.S. Pat. Nos. 6,368,819 and 6,753,170 describe a solvent and co-solvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented microorganisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Biomass recovered from the bioreactor may undergo anaerobic digestion to produce a biomass product, preferably methane. This biomass product may be used as a feedstock for the steam reforming process or used to produce supplemental heat to drive one or more of the reactions defined herein.

EXAMPLES

Materials and Methods for Start Up

Media

| Bioreactor Media component | Concentration per 1.0 L of media |
|---|---|
| $MgCl_2 \cdot 6H_2O$ | 0.1 g |
| $CaCl_2 \cdot 2H_2O$ | 0.15 g |
| KCl | 0.15 g |
| NaCl | 0.12 g |
| 85% H3PO4 | 0.38 mL |
| Metal Mix 1 (Fe 0.1M, Ni 0.005M, Zn 0.005M) | 1 mL |
| Metal Mix 2 (0.01M B, Mn, Co, Se, Mo) | 0.2 mL |
| 0.01M Tungsten Solution | 0.2 mL |
| Rezasurin (2 g/L) | 0.5 mL |
| B-Vitamin Solution (LS03) | 10 mL |
| Cysteine | 2.5 g |

| Serum Bottle Media component | Concentration per 1.0 L of media |
|---|---|
| $MgCl_2 \cdot 6H_2O$ | 0.5 g |
| $CaCl_2 \cdot 2H_2O$ | 0.37 g |
| KCl | 0.15 g |
| NaCl | 0.12 g |
| 85% H3PO4 | 0.5 mL |
| $CH_3COONH_4$ | 1 g |
| Metal Mix 1 (Fe 0.1M, Ni 0.005M, Zn 0.005M) | 1 mL |
| Metal Mix 2 (0.01M B, Mn, Co, Se, Mo) | 0.2 mL |
| 0.01M Tungsten Solution | 0.2 mL |
| Rezasurin (2 g/L) | 0.75 mL |
| B-Vitamin Solution (LS03) | 10 mL |
| Cysteine | 0.5 g |
| Yeast Extract | 1 g |

| B-Vitamin Solution (LS03) | Per L of stock |
|---|---|
| Thiamine HCl | 50 mg |
| Riboflavin | 50 mg |
| Nicotinic Acid | 50 mg |
| Pantothenic Acid | 50 mg |
| Pyridoxine HCl | 10 mg |
| Biotin | 20 mg |
| Folic Acid | 20 mg |
| 4-Aminobenzoic Acid | 50 mg |
| Cyanocobalamin | 50 mg |
| Lipoic Acid | 50 mg |
| Distilled Water | To 1 L |

| Metal Mix 1 | Per L of Stock |
|---|---|
| $FeCl_2 \cdot 4H_2O$ | 19.35 g |
| $NiCl_2 \cdot 6H_2O$ | 1.19 g |
| $ZnCl_2$ | 0.69 g |

| Metal Mix 2 | Per L of Stock |
|---|---|
| $CoCl_2 \cdot 6H_2O$ | 2.38 g |
| $HBO_4$ | 0.62 g |
| $MnCl_2 \cdot 4H_2O$ | 1.98 g |
| $NaMoO_4 \cdot 2H_2O$ | 2.42 g |
| $Na_2SeO_3$ | 1.73 g |
| $Na_2WO_4 \cdot 2H_2O$ | 3.29 |

Fermentation in Serum Bottle

Incubation was performed by injecting 1 mL of a *Clostridium autoethanogenum* freeze dried stock in a 234 mL anaerobic serum bottle containing 50 mL of the media. The headspace of serum bottle was flushed with 30 psi RMG. It was stored on a shaking incubator at maintained temperature of 37° C. After two days of incubation or when optical density of the culture reach 0.2, it was sub cultured into 8 serum bottles.

Fermentation in Bioreactor

Examples 1 and 2

The media was prepared by mixing all the ingredients in 5 L distilled water with the exception of B-Vitamin Solution and Cysteine. Ten liters CSTR reactor was prepared and 4.5 L of the media solution was placed inside. The reactor was then sterilized in autoclave for 30 mins at 121° C. After autoclaving, the reactor was allowed to cool, maintained at 37° C. and made anaerobic by constant flow of $N_2$ gas and agitation at 200 rpm. Once cool, the B-Vitamin and cysteine solutions were added using 0.2 μm filtered syringes. The pH of the solution was then adjusted and maintained at 5.3 using 5 M $NH_4OH$ solution.

Two hours before inoculation, the $N_2$ gas was switched to 100 ml/min RMG and the media was further reduced using 0.2 M $Cr^{2+}$ solution to −250 mV. It was inoculated with 400 mL of *Clostridium autoethanogenum* serum bottle culture. The fermentation started as a batch with gentle increase of gas and agitation overtime. Two days after inoculation, the culture was turned continuous, still with gentle pushing, and finally kept stable at 550 ml/min RMG and 400 rpm agitation.

Fermentation in Bioreactor

Example 3

Two 2-liter reactors were filled with 1.5 L of media containing all metals, phosphoric acid, B-Vitamins (as specified in the tables above). The media was then degassed using an industrial gas having the following composition; approximately 50% CO, 20% $CO_2$, 28% $N_2$ and 2% $H_2$. 0.12 M $(NH_4)_2SO_3$ (pH 6.0) was added at a rate of 0.2 mL/h to deliver sulphur into the media before inoculation. The ORP (Ag/AgCl electrode) was further adjusted to −200 mV with 0.2M $Cr^{2+}$ before inoculation with 200 mL culture from a continuously running seed fermenter with a biomass of approximately 2 g/L. pH, ORP, gas uptake and $H_2S$ in the headspace were closely monitored over the next hours to ensure a successful start-up. The pH was controlled via managing the optimal delivery of gas to the culture and additionally backed up by automatic pH control (at 5.0) via 5M $NH_4OH$. For the first 24 hours the culture is a batch ferment and then switched to continuous mode by delivering media (2 mM NaCl, 2 mM KCl, 0.5 mM $MgCl_2$, 1 mM $CaCl_2$, B-Vitamins, 5 mM phosphoric acid, metal mix) at a rate to achieve a dilution rate between 2 and 3 and at the same time delivering $(NH_4)_2SO_3$ and antifoam at the appropriate rates.

0.12M $(NH_4)_2SO_3$ (pH to 6.0 with conc. HCl) as sulphur source–flow rate adjusted so that $H_2S$ in headspace<100 ppm Antifoam (Poly(propylene glycol)-block-poly(ethylene glycol)-block-poly(propylene glycol) (CAS 9003-11-6) (10 µL/h)

The experiment in the 1.5 L reactors was carried out as a 2-fermenter system. Both reactors featured cell recycling. Hollow fibre membrane cartridges with a pore size of 0.1 µm are used for cell recycling. When reactors are joined to a 2-fermenter system the permeate resulting from cell recycling and the waste are transferred directly into the downstream fermenter. Thus the ratio between permeate and waste remains an estimate based on the dialled—in flow rates.

Example 1

$H_2SO_3$ as a Sulphur Source

Background

This experiment was performed on a stable continuously running seed fermenter in a single reactor system. The main purpose of the seed fermenter was to provide start-up inoculum for other bioreactors fermentation. As such this fermenter was kept stable and undersupplied with low gas supply and agitation. A seed fermenter normally runs for approximately one to two months before being stopped and restarted (to reduce the risk of contamination). The experiments were performed on the culture after two months of continual stable running time. The profiles of a seed fermenter are different from those of high performance fermentation systems.

The aim for these experiments was to find alternative sulphur source for *C. autoethanogenum* and other carboxydotrophic acetogenic microorganisms. It has been discovered that *C. autoethanogenum* is capable of utilizing a sulphur source from $Na_2S$ (either by dripping the solution straight into fermenter or dripping the solution into a closed container filled with $H_3PO_4$ and supplying the $H_2S$ released into the fermenter). *C. autoethanogenum* is also able to consume cysteine and release $H_2S$ and in the past $S_8$ was proven to be effective as well. These experiments focused on $H_2SO_3$ because it has advantages compared to the current sulphur source ($Na_2S$ or cysteine). $H_2SO_3$ is toxic to most microorganisms so it could act as a disinfectant as well as sulphur source. Furthermore, $SO_2$ gas is a waste product of coal power plants and it had caused environmental problem in form of acid rains. Since then, coal power plants have to filter their sulphur emission and international treaties are made to reduce the said pollution.

Method:

~0.6 M of $SO_2$ in water solution was pumped into 10 L fermenter using syringe pump. The performance indicators are $H_2S$ in headspace and $H_2$ & CO uptake. A working sulphur source should produce $H_2S$ and give stable $H_2$ & CO uptake. $H_2$ uptake is an early indicator of the health state of the microbes.

Results:

Approximately 0.6 M concentration with 1 ml/hr pump rate gave excessive amount of $H_2S$ in headspace (approximately 600 ppm). To reduce the $H_2S$ produced, the solution was diluted 10× and pump rate was adjusted to achieve the desirable value.

Figure 1:
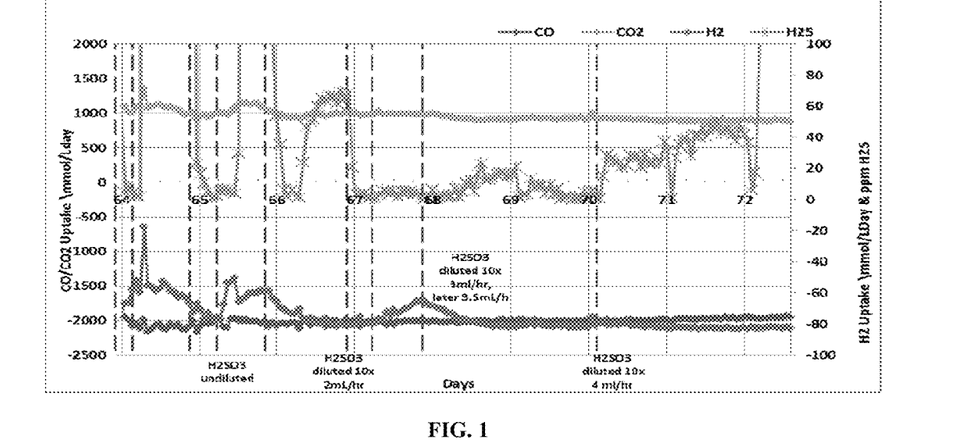
FIG. 1 shows $H_2$ uptake and $H_2S$ production in a *C. autoethanogenum* fermentation using $H_2SO_3$ as a sulphur source.

FIG. 1 shows the Hydrogen uptake and $H_2S$ production in the bioreactor.

At 2 ml per hour pump rate the culture produced almost no $H_2S$ and the H2 uptake was unstable and decreasing.

At 3 ml per hour pump rate the amount of H2S in the headspace was around 60-70 ppm $H_2S$. When the pump rate was increased to 3.5 ml per hour the amount of $H_2S$ fluctuated from around 20 ppm $H_2S$ to almost zero. The $H_2$ uptake was very stable. Increasing the pump rate to 4 ml per hour resulted in excessive amounts of $H_2S$.

Example 2

$(NH_4)HSO_3$ as a Sulphur Source

Background

This experiment was a continuation of the $H_2SO_3$ experiment. $H_2SO_3$ is very acidic and in form of $SO_2$ in water which in its current pH releases toxic $SO_2$ gas that may cause health & safety problems. Separate experiment of storing this solution in an IV bag (normal method of supplying $Na_2S$ into a fermenter) showed that even though the bag was not damaged, it was inflated due to accumulation of $SO_2$ gas.

To provide a safer solution, $SO_2$ in water ($H_2SO_3$) had its pH adjusted to 6 using concentrated $NH_4OH$ which produce safe and almost no smell $(NH_4)HSO_3$. This solution was then tested on a seed fermenter.

Method:

Approximately 0.6 M of $SO_2$ in water solution is reacted with 28% $NH_4OH$ to bring the pH up to 6 and 10× diluted. The solution is then supplied to the fermenter using syringe pump.

Figure 2:
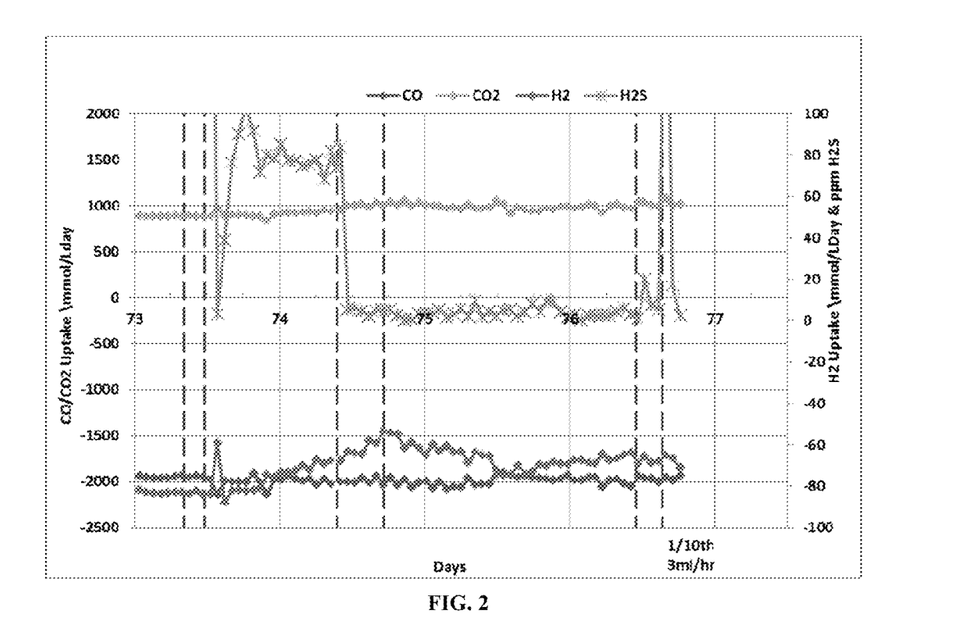
FIG. 2 shows $H_2$ uptake and $H_2S$ production in a *C. autoethanogenum* fermentation using $(NH_4)HSO_3$ as a sulphur source.

Results:

FIG. 2 shows the $H_2$ uptake and $H_2S$ levels in the bioreactor. As shown in FIG. 2; 4 ml per hour of undiluted solution gave excessive amount of $H_2S$. A rate of 4 ml per hour of diluted solution gave approximately 80 ppm of $H_2S$.

A rate of 2 ml per hour of 1/10 diluted solution gave minimum amount of $H_2S$ however the $H_2$ uptake was decreasing. A rate of 3 ml per hour of 1/10 diluted solution resulted in low levels of $H_2S$ and a stable $H_2$ uptake.

Example 3

$(NH_4)_2SO_3$ as a Sulphur Source

Figure 6:
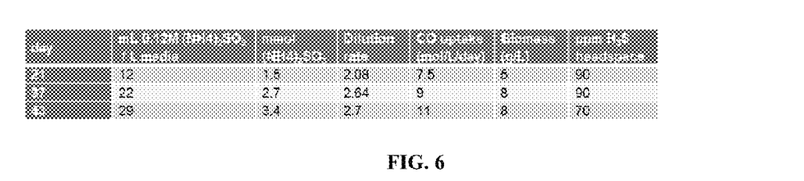
FIG. 6 shows $(NH_4)_2SO_3$ addition in a first reactor, linked to other process parameters.
Figure 7:
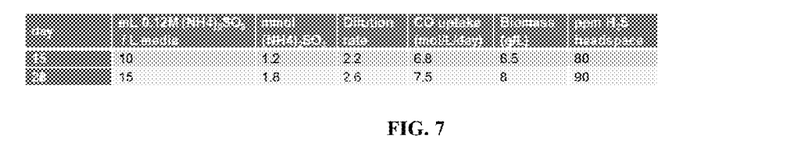
FIG. 7 shows $(NH_4)_2SO_3$ addition in a second reactor linked to other process parameters.

Method:

$(NH_4)_2SO_3$ was used as sulphur source in a two-fermenter system. A 0.12 M $(NH_4)_2SO_3$ solution is prepared and the pH adjusted to 6.0 with concentrated HCl. This solution can be used at similar rates as a 0.5M $Na_2S$ solution. The dosing is adjusted to keep the $H_2S$ in the headspace below 100 ppm. Higher concentrations of $H_2S$ in the headspace are indicative of $SO_2$ levels in the broth that could potentially harm the culture. FIGS. 6 and 7 show how at higher concentrations of biomass, and higher dilution rates and gas rates the concentration of $(NH_4)_2SO_3$ required to maintain $H_2S$ at target levels increases. At the time of inoculation one has to be particularly careful not to add too much $(NH_4)_2SO_3$. $H_2S$ as an indicator is only available after inoculation. $H_2S$ will not be present in the headspace before inoculation. From this experiment it has been shown that the optimum concentration for $(NH_4)_2SO_3$ is between 1 and 3.5 mmol for a continuous high performance culture, depending on biomass, gas flow and dilution rate. At the time of inoculation the concentration should be less than 0.3 mmol.

Figure 3:
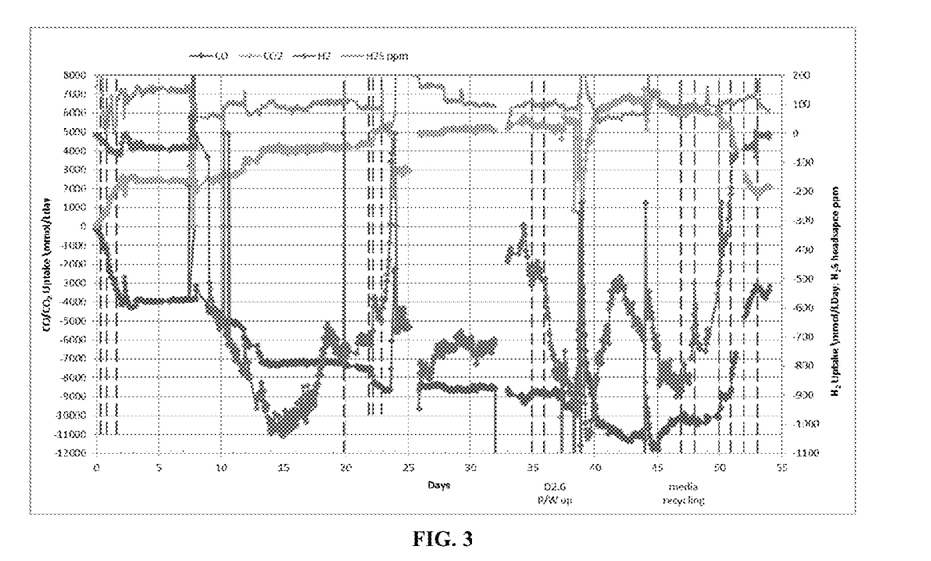
FIG. 3 shows gas uptake and $H_2S$ concentration in the first reactor of a two reactor system.
Figure 4:
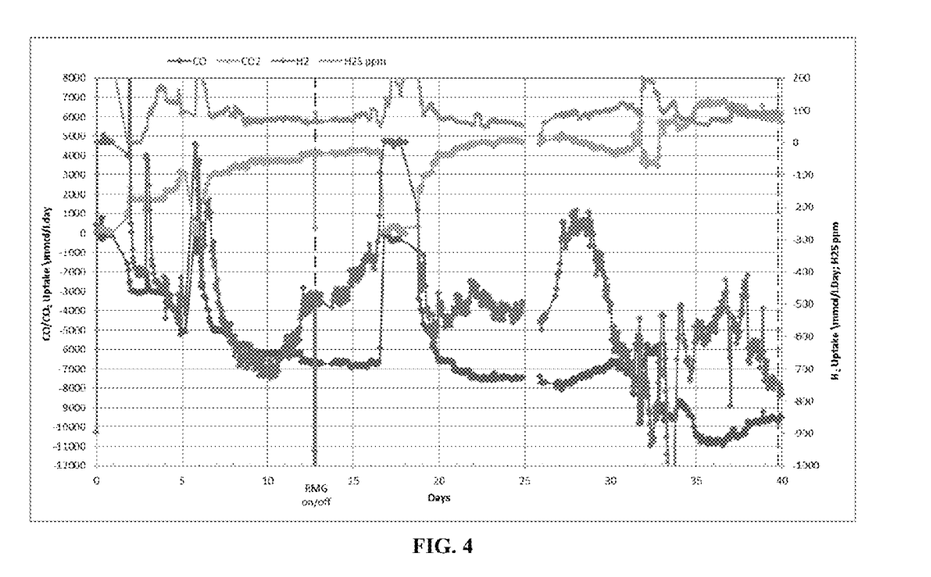
FIG. 4 shows gas uptake and $H_2S$ concentration in the second reactor of a two reactor system

Results:

$(NH_4)_2SO_3$ was added to a solution at pH6 for use as an alternative sulphur source. The $(NH_4)_2SO_3$ was added to the fermentation at the same rate as a 0.5M $Na_2S$ solution. During the course of the experiment it was shown to be desirable to maintain the concentration of $(NH_4)_2SO_3$ in solution, such that the amount of $H_2S$ in the headspace of the reactor was maintained at a concentration of less than 100 ppm. As shown in FIGS. 3 and 4, the fermentation was maintained in a stable manner using $(NH_4)_2SO_3$ for approximately 40 day, demonstrating the effectiveness of $(NH_4)_2SO_3$ as an alternative sulphur source Stable continuous fermentation using $(NH_4)_2SO_3$ as the sulphur source for the microorganism was demonstrates whilst maintaining a desire $(NH_4)_2SO_3$ concentration in the fermentation broth of between 1 and 3.5 mmol, and maintaining a H2S concentration in the headspace of less than 100 ppm.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

Where reference has been made in the foregoing description to integers having known equivalents thereof, those integers are herein incorporated as if individually set forth.

Furthermore, titles, heading, or the like are provided to enhance the reader's comprehension of this document, and should not be read as limiting the scope of the present invention. The entire disclosures of all applications, patents and publications cited above and below, if any, are herein incorporated by reference.

The reference to any prior art in this specification is not, and should not be taken as, an acknowledgement or any form of suggestion that that prior art forms part of the common general knowledge in the field of endeavour in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method of producing at least one product by microbial fermentation, the method comprising;
   a) providing a gaseous substrate comprising CO to a bioreactor comprising a culture of at least one carboxydotrophic microorganisms in a liquid nutrient medium comprising a sulphur source;
   b) anaerobically fermenting the substrate to produce at least one product selected from the group consisting of alcohols, acids and mixtures thereof;
   c) converting the sulphur source to $H_2S$ in a headspace of the bioreactor;
   d) adjusting the concentration of the sulphur source in the liquid nutrient medium to maintain the concentration of $H_2S$ in the headspace within a desired range; and
   e) recovering the at least one product.

2. The method of claim 1 wherein the liquid nutrient medium comprises a sulphur source selected from the group consisting of SO2, H2SO3, Na2S2O4, S8, Na2S, NaHS, cysteine, NH4SO3 or (NH4)2SO3.

3. The method of claim 2 wherein the sulphur source is sulphurous acid.

4. The method of claim 3 wherein the concentration of sulphurous acid in the liquid nutrient medium is maintained between 1 and 3.5 mmol.

5. The method of claim 1 wherein the concentration of $H_2S$ in the headspace is maintained between about 1 ppm and about 100 ppm.

6. The method of claim 1 wherein the one or more carboxydotrophic microorganisms is selected from the group consisting of *Clostridium autoethanogenum*, *Clostridium ljungdahlii*, *Clostridium ragsdalei*, *Clostridium coskatii* and *Clostridium carboxydivorans*.

7. The method of claim 6 wherein the carboxydotrophic microorganism is *Clostridium autoethanogenum*.

8. The method of claim 6 wherein the carboxydotrophic microorganism is *Clostridium autoethanogenum* strain deposited at the German Resource Centre for Biological Material (DSMZ) under the identifying deposit number DSM19630.

9. The method of claim 6 wherein the carboxydotrophic microorganism is *Clostridium autoethanogenum* strain deposited at the German Resource Centre for Biological Material (DSMZ) under the identifying deposit number DSM 23693.

10. The method of claim 1 wherein the sulphur source is a waste product of an industrial process.

11. The method of claim 1 wherein the sulphur source is a waste product of a coal manufacturing process.

* * * * *